United States Patent [19]

Beard et al.

[11] 4,031,234
[45] June 21, 1977

[54] 1,5(6)-DISUBSTITUTED BENZIMIDAZOLE-2-CARBAMATE DERIVATIVES HAVING ANTHELMINTIC ACTIVITY

[75] Inventors: Colin C. Beard, Palo Alto; John A. Edwards, Los Altos; John H. Fried, Palo Alto, all of Calif.

[73] Assignee: Syntex (U.S.A.) Inc., Palo Alto, Calif.

[22] Filed: June 18, 1976

[21] Appl. No.: 697,499

Related U.S. Application Data

[60] Division of Ser. No. 605,704, Aug. 18, 1975, Pat. No. 3,993,769, which is a division of Ser. No. 473,865, May 28, 1974, Pat. No. 3,929,822, which is a continuation-in-part of Ser. No. 417,963, Nov. 21, 1973, Pat. No. 3,929,821, which is a continuation-in-part of Ser. No. 319,299, Dec. 29, 1972, abandoned.

[52] U.S. Cl. .............................................. 424/273
[51] Int. Cl.² ...................................... A61K 31/415
[58] Field of Search ................................. 424/273

[56] References Cited

UNITED STATES PATENTS

| | | | |
|---|---|---|---|
| 3,641,048 | 2/1972 | Dittmar | 424/273 |
| 3,657,267 | 4/1972 | Van Gelder et al. | 424/273 |

Primary Examiner—Sam Rosen
Attorney, Agent, or Firm—Joseph I. Hirsch; William B. Walker

[57] ABSTRACT

This application relates to 1,5(6)-disubstituted benzimidazole-2-carbamate derivatives represented by the following formula:

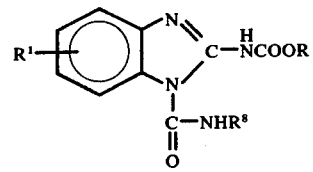

where
R is lower alkyl having 1 to 4 carbon atoms; $R^1$ is $-SOR^2$, $-SR^5$, $-OR^5$ or $M'(CH_2)_nMR^7$; $R^2$ is lower alkyl having from 1 to 6 carbon atoms, cycloalkyl having 3 to 7 carbon atoms, lower alkenyl or lower alkynyl having 3 to 6 carbon atoms, or aralkyl or aryl; $R^5$ is lower alkenyl, lower alkynyl or aralkyl; $R^7$ is lower alkyl having 1 to 4 carbon atom, or aryl; M and M' are independently O, S,

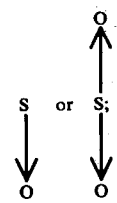

$n$ is 1–4; and $R^8$ is lower alkyl having 1 to 12 carbon atoms optionally substituted with a $-COOR$ group where R is lower alkyl having 1 to 4 carbon atoms, aryl or aralkyl. The $R^1$ substitution is at the 5(6)-position.

The compounds are useful as pesticides, particularly as anthelmintic and antifungal agents.

36 Claims, No Drawings

1,5(6)-DISUBSTITUTED BENZIMIDAZOLE-2-CARBAMATE DERIVATIVES HAVING ANTHELMINTIC ACTIVITY

REFERENCE TO PARENT APPLICATIONS

This application is a division of application Ser. No. 605,704, filed Aug. 18, 1975, now U.S. Pat. No. 3,993,769, which, in turn, is a division of application Ser. No. 473,865, filed May 28, 1974, now U.S. Pat. No. 3,929,822, which is, in turn a continuation-in-part application of application Ser. No. 417,963, filed Nov. 21, 1973, now U.S. Pat. No. 3,929,821, which, in turn, is a continuation-in-part application of application Ser. No. 319,299, filed Dec. 29, 1972, now abandoned.

FIELD OF THE INVENTION

This invention relates to novel chemical compounds. More particularly, this invention relates to novel 1,5(6)-disubstituted benzimidazole-2-carbamate derivatives having pesticidal, particularly anthelmintic, activity.

BACKGROUND OF THE INVENTION

Anthelmintically active benzimidazole-2-carbamate derivatives either unsubstituted at the 5(6)-position or substituted with different substituents than those described and claimed herein are known in this art (for example, see U.S. Pat. Nos. 3,480,642; 3,573,321; 3,574,845; 3,578,676; and 3,595,870). Related fungicidal compounds are also shown in U.S. Pat. Nos. 2,933,504 and 3,010,968.

SUMMARY OF THE INVENTION

The novel 1,5(6)-disubstituted benzimidazole-2-carbamate derivatives of the present invention can be represented by the following formula:

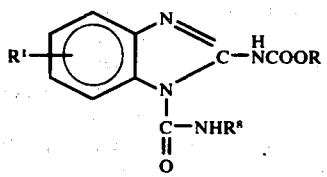

(I)

where
R is lower alkyl having 1 to 4 carbon atoms; $R^1$ is $-SOR^2$, $-SR^5$, $-OR^5$ or $M'(CH_2)_nMR^7$; $R^2$ is lower alkyl having from 1 to 6 carbon atoms, cycloalkyl having 3 to 7 carbon atoms, lower alkenyl or lower alkynyl having 3 to 6 carbon atoms, or aralkyl or aryl; $R^5$ is lower alkenyl, lower alkynyl or aralkyl; $R^7$ is lower alkyl having 1 to 4 carbon atoms or aryl; M and M' are independently O, S,

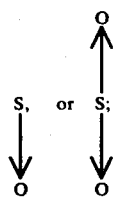

n is 1–4; and $R^8$ is lower alkyl having 1 to 12 carbon atoms optionally substituted with a —COOR group where R is lower alkyl having 1 to 4 carbon atoms, aryl or aralkyl. The $R^1$ substitution is at the 5(6)-position.

As used in this specification and claims, the term "lower alkyl" refers to both straight and branched chain alkyl groups having either a total of from 1 through 4 carbon atoms, from 1 through 6 carbon atoms, or 1 through 12 carbon atoms, as the case may be, and thus includes primary, secondary and tertiary alkyl groups. Typical lower alkyls include, for example, methyl, ethyl, n-propyl, isopropyl, n-butyl, isobutyl, t-butyl, n-amyl, n-hexyl, octyl, nonyl, decyl, dodecyl, and the like. The term "cycloalkyl" refers to cyclic hydrocarbon groups having from 3 to 7 carbon atoms such as, for example, cyclopropyl, cyclopentyl, cyclohexyl, and the like. The term "lower alkenyl" refers to an unsaturated hydrocarbon group having from 3 to 6 carbon atoms and a single carbon-carbon double bond, provided that the double bond cannot be on the α-carbon atom. Typical alkenyl groups include, for example, 2-propenyl, 2-butenyl, 3-butenyl, and the like. The term "lower alkynyl" refers to an unsaturated hydrocarbon group having from 3 to 6 carbon atoms, and a single carbon-carbon triple bond, provided also that the triple bond cannot be on the α-carbon atom. Typical alkynyl groups include, for example, 2-propynyl, 2-butynyl, 3-butynyl, and the like. An alkyl, alkenyl or alkynyl group of the $R^1$ moiety can be optionally substituted with one or more radicals, for example, thiocyanato; alkoxy, such as methoxy; aryl, such as phenyl; aroyl, such as benzoyl; hydroxy; cycloalkyl; halo; cyano; or nitro radicals. The term "alkoxy" refers to the group having the formula RO— wherein R is a lower alkyl as defined above. Typical alkoxy groups include, for example, methoxy, ethoxy, t-butoxy and the like. The term "halo" refers to iodo, bromo, chloro, fluoro groups. The term "aryl" refers to an aromatic hydrocarbon group, such as phenyl. The term "aralkyl" refers to an aryl substituted alkyl group, such as, for example, benzyl or phenethyl. The aryl or aralkyl groups can be optionally substituted with one or more lower alkyl, alkoxy, halo or nitro radicals.

The compounds of the present invention, and the nontoxic salts thereof formed with pharmaceutically acceptable inorganic or organic acids, possess broad spectrum activity against parasites of mammals, including both mature and immature parasitic forms, as represented for example, by the genera Trichostronglylus, Haemonchus, Ostertagia, Cooperia, Nematodirus, and Stronglyoides, and specifically, for example against Nematospiroides dubius, Hymenolepis Nana, Syphacia obvelata, and/or Aspiculuris tetraptera. In particular, these compounds are found to exhibit high activity against various helminthic infections of the intestinal tract of economically important animals, coupled with low systemic toxicity to the host animal.

The compounds of the present invention are also useful as antifungal agents, particularly as systemic fungicides for controlling fungal diseases of plants of economic importance.

In addition to the stated anthelmintic and antifungal properties, certain compounds of the present invention are also useful as intermediates in the preparation of further compounds of this invention. For example, the 5(6)-thio compounds (i.e., where $R^1$ is $-SR^5$) can be prepared and then utilized as starting materials for the preparation of the corresponding 5(6)-sulfinyl compounds.

Where the compound has a basic moiety, the term nontoxic salts as used herein refers to those pharmaceutically acceptable salts of the compounds of this invention which do not adversely affect the antifungal or anthelmintic properties of the basic compound, such as those salts conventionally used in the art. Such nontoxic salts include, for example, salts of inorganic acids such as, for example, sulfuric, sulfonic, sulfamic, nitric, phosphoric, hydrochloric acids and the like, and salts of organic acids such as, for example, acetic, citric, lactic, palmitic, tartaric, succinic, maleic, benzoic acids and the like. Where the compound has an acidic moiety, the non-toxic salts include cation salts, such as, for example, the salts of sodium, potassium, ammonium, and the like.

The amount of the compound to be administered will depend upon the actual compound utilized, and upon the weight of animal being treated. In general, however, the daily dosage level will usually be between about 5 mg/kg and 100 mg/kg of body weight of the animal being treated. The active ingredient is adapted to be administered to the animal by mixing it with the diet of the animal, as with a feed mix, or formulating it with a non-toxic carrier to give anthelmintic compositions. The carrier may be an orally ingestible container for the active ingredient such as, for example, a gelatin capsule, or it may be an excipient of the kind normally used in medicaments of this character, including maize starch, terra alba, lactose, sucrose, calcium phosphate, gelatin, stearic acid, pectin or the like. Examples of suitable liquid carriers are peanut oil, sesame oil and water.

A wide variety of pharmaceutical forms can be employed in those cases wherein the medicament is not admixed with the feed. Thus, if a solid carrier is used, the compound can be administered in tablet or capsule form. If a liquid carrier is used, the medicament may be in the form of a soft gelatin capsule or in a liquid suspension.

The compounds of the present invention are prepared by reacting a compound of the formula:

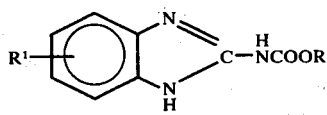

(II)

with a substituted isocyanate of the formula OCNR$^8$, where R, R$^1$ and R$^8$ are as defined above, in an inert organic solvent, for example tetrahydrofuran, at about 0° to about 40° C, generally about room temperature, for about ½ hour to about 96 hours, generally about 20 to 48 hours. Thereafter, the product is separated and purified by any suitable procedure. For example, typical separation procedures include filtration, extraction, evaporation, and typical purification procedures include crystallization, and both thin-layer and column chromatography. Optimum separation and isolation procedures can be obtained for any given step by routine experimentation as will be apparent to those skilled in this art. The product so obtained is a mixture of the 1,5-disubstituted and 1,6-disubstituted compounds, wherein, with respect to each compound, the R, R$^1$ and R$^8$ substitutents are the same.

The compounds of Formula II above, and methods for the preparation thereof, are described in copending application Ser. No. 417,963, filed Nov. 21, 1973, and abandoned application Ser. No. 319,299, filed Dec. 29, 1972. The entire subject matter of both of the aforementioned applications are incorporated herein by reference.

Exemplary of the compounds of the present invention as represented by structural formula I above, are the following illustrative compounds:

1-methylcarbamoyl-5(6)-phenylsulfinyl-2-carbomethoxyaminobenzimidazole;

1-ethoxycarbonylmethylcarbamoyl-5(6)-phenylsulfinyl-2-carbomethoxyaminobenzimidazole;

1-ethylcarbamoyl-5(6)-phenylsulfinyl-2-carbomethoxyaminobenzimidazole;

1-n-propylcarbamoyl-5(6)-phenylsulfinyl-2-carbomethoxyaminobenzimidazole;

1-i-propylcarbamoyl-5(6)-phenylsulfinyl-2-carbomethoxyaminobenzimidazole;

1-n-butylcarbamoyl-5(6)-phenylsulfinyl-2-carbomethoxyaminobenzimidazole;

1-n-hexylcarbamoyl-5(6)-phenylsulfinyl-2-carbomethoxyaminobenzimidazole;

1-phenylcarbamoyl-5(6)-phenylsulfinyl-2-carbomethoxyaminobenzimidazole;

1-benzylcarbamoyl-5(6)-phenylsulfinyl-2-carbomethoxyaminobenzimidazole;

1-phenethylcarbamoyl-5(6)-phenylsulfinyl-2-carbomethoxyaminobenzimidazole;

1-methylcarbamoyl-5(6)-methoxymethylsulfinyl-2-carbomethoxyaminobenzimidazole;

1-ethoxycarbonylmethylcarbamoyl-5(6)-methoxymethylsulfinyl-2-carbomethoxyaminobenzimidazole;

1-ethylcarbamoyl-5(6)-methoxymethylsulfinyl-2-carbomethoxyaminobenzimidazole;

1-n-butylcarbamoyl-5(6)-phenoxyethoxy-2-carbomethoxyaminobenzimidazole;

1-n-propylcarbamoyl-5(6)-methoxymethylsulfinyl-2-carbomethoxyaminobenzimidazole;

1-i-propylcarbamoyl-5(6)-methoxymethylsulfinyl-2-carbomethoxyaminobenzimidazole;

1-n-butylcarbamoyl-5(6)-methoxymethylsulfinyl-2-carbomethoxyaminobenzimidazole;

1-n-hexylcarbamoyl-5(6)-methoxymethylsulfinyl-2-carbomethoxyaminobenzimidazole;

1-phenylcarbamoyl-5(6)-methoxymethylsulfinyl-2-carbomethoxyaminobenzimidzole;

1-phenethylcarbamoyl-5(6)-methoxymethylsulfinyl-2-carbomethoxyaminobenzimidazole;

1-methylcarbamoyl-5(6)-naphth-2'-ylsulfinyl-2-carbomethoxyaminobenzimidazole;

1-n-butylcarbamoyl-5(6)-napth2'-ylsulfinyl-2-carbomethoxyaminobenzimidzole;

1-methylcarbamoyl-5(6)-p-fluorophenylsulfinyl-2-carbomethoxyaminobenzimidazole;

1-n-butylcarbamoyl-5(6)-p-fluorophenylsulfinyl-2-carbomethoxyaminobenzimidazole;

1-methylcarbamoyl-5(6)-trifluoromethylmethylsulfinyl-2-carbomethoxyaminobenzimidazole;

1-n-butylcarbamoyl-5(6)-trifluoromethylmethylsulfinyl-2-carbomethoxyaminobenzimidazole;

1-methylcarbamoyl-5(6)-ethylsulfinyl-2-carbomethoxyaminobenzimidazole;

1-n-butylcarbamoyl-5(6)-ethylsulfinyl-2-carbomethoxyaminobenzimidazole;

1-n-butylcarbamoyl-5(6)-methoxyethylsulfinyl-2-carbomethoxyaminobenzimidazole;

1-methylcarbamoyl-5(6)-n-propylsulfinyl-2-carbomethoxyaminobenzimidazole;

1-n-butylcarbamoyl-5(6)-n-propylsulfinyl-2-carbomethoxyaminobenzimidazole;
1-methylcarbamoyl-5(6)-n-butylsulfinyl-2-carbomethoxyaminobenzimidazole;
1-n-butylcarbamoyl-5(6)-n-butylsulfinyl-2-carbomethoxyaminobenzimidazole;
1-methylcarbamoyl-5(6)-(prop-2-en-1-ylsulfinyl)-2-carbomethoxyaminobenzimidazole;
1-n-butylcarbamoyl-5(6)-(prop-2-en-1-ylsulfinyl)-2-carbomethoxyaminobenzimidazole;
1-methylcarbamoyl-5(6)-(prop-2-en-1-ylthio)-2-carbomethoxyaminobenzimidazole;
1-n-butylcarbamoyl-5(6)-(prop-2-en-1-ylthio)-2-carbomethoxyaminobenzimidazole;
1-methylcarbamoyl-5(6)-(prop-2-yn-1-ylsulfinyl)-2-carbomethoxyaminobenzimidazole;
1-n-butylcarbamoyl-5(6)-(prop-2-yn-1-ylsulfinyl)-2-carbomethoxyaminobenzimidazole;
1-methylcarbamoyl-5(6)-(prop-2-yn-1-ylthio)-2-carbomethoxyaminobenzimidazole;
1-n-butylcarbamoyl-5(6)-(prop-2-yl-1-ylthio)-2-carbomethoxyaminobenzimidazole;
1-methylcarbamoyl-5(6)-methoxymethylthio-2-carbomethoxyaminobenzimidazole;
1-n-butylcarbamoyl-5(6)-methoxymethylthio-2-carbomethoxyaminobenzimidazole;
1-n-butylcarbamoyl-5(6)-(2,2,3,3-tetrafluoropropylsulfinyl)-2-carbomethoxyaminobenzimidazole;
1-methylcarbamoyl-5(6)-methylthiomethoxy-2-carbomethoxyaminobenzimidazole;
1-n-butylcarbamoyl-5(6)-methylthiomethoxy-2-carbomethoxyaminobenzimidazole;
1-methylcarbamoyl-5(6)-methylsulfinylmethoxy-2-carbomethoxyaminobenzimidazole;
1-n-butylcarbamoyl-5(6)-methylsulfinylmethoxy-2-carbomethoxybenzimidazole;
1-methylcarbamoyl-5(6)-methoxymethoxy-2-carbomethoxyaminobenzimidazole;
1-n-butylcarbamoyl-5(6)-methoxymethoxy-2-carbomethoxyaminobenzimidazole;

and the corresponding 2-carbethoxyamino-, 2-carbopropoxyamino-, and 2-carbobutoxyamino compounds.

Of these compounds, the 1-n-butylcarbamoyl compounds, including 1n-butylcarbamoyl-5(6)-phenylsulfinyl-2-carbomethoxyaminobenzimidazole and 1-n-butylcarbamoyl-5(6)-methoxymethylsulfinyl-2-carbomethoxyaminobenzimidazole, are presently preferred because they have shown substantial activity against certain of the helminths specifically referred to above.

DESCRIPTION OF THE SPECIFIC EMBODIMENTS

The following specific description is given to enable those skilled in this art to more clearly understand and practice the present invention. It should not be considered as a limitation upon the scope of the invention but merely as being illustrative and representative thereof.

EXAMPLE I

A suspension of 1.41 g. of 5(6)-methoxymethylsulfinyl-2-carbomethoxyaminobenzimidazole in 140 ml. of tetrahydrofuran is treated with 2.4 g. of n-butylisocyanate at room temperature (20°–25° C). After 24 hours, 140 ml. of methylene chloride is added and the solution concentrated under vacuum at 20°–30° C. The resulting precipitate is filtered off, washed with tetrahydrofuran and dried to afford 1-n-butylcarbamoyl-5(6)-methoxymethylsulfinyl-2-carbomethoxyaminobenzimidazole.

EXAMPLE II

A suspension of 0.63 g. of 5(6)-phenylsulfinyl-2-carbomethoxybenzimidazole in 50 ml. of tetrahydrofuran is treated at 20°–25° C with 0.5 g. of phenylisocyanate. After 20 hours, the solution is concentrated under vacuum at 20°–30° C and the residue triturated with acetone and filtered to afford 1-phenylcarbamoyl-5(6)-phenylsulfinyl-2-carbomethoxyaminobenzimidazole.

EXAMPLE III

A suspension of 0.95 g. of 5(6)-phenylsulfinyl-2-carbomethoxyaminobenzimidazole in 50 ml. of tetrahydrofuran is treated at 20°–25° C with 0.7 g. of n-butylisocyanate. After 24 hours, the solution is concentrated under vacuum at 20°–30° C. The residue is triturated with methanol, filtered, and washed with methanol to afford 1-n-butylcarbamoyl-5(6)-phenylsulfinyl-2-carbomethoxyaminobenzimidazole.

EXAMPLE IV

A slurry of 0.31 g. of 5(6)-phenylsulfinyl-2-carbomethoxyaminobenzimidazole in 18 ml. of tetrahydrofuran is treated with 0.26 g. of ethoxycarbonylmethylisocyanate at 20°–25° C for 24 hours. Concentration of the solvent under vacuum and filtration affords 1-ethoxycarbonylmethylcarbamoyl-5(6)-phenylsulfinyl-2-carbomethoxyaminobenzimidazole.

EXAMPLE V

A suspension of 0.95 g. of 5(6)-phenylsulfinyl-2-carbomethoxyaminobenzimidazole in 35 ml. of tetrahydrofuran is treated with 0.4 g. of methylisocyanate at 20°–25° C. After 48 hours, the product is filtered off and dried under vacuum to afford 1-methylcarbamoyl-5(6)-phenylsulfinyl-2-carbomethoxyaminobenzimidazole.

In similar manner to the Examples above, using the corresponding 2-carbethoxyamino-, 2-carbopropoxyamino-, and 2-carbobutoxyamino compounds, 5(6)-phenylsulfinyl-2-carbomethoxyaminobenzimidazole, 5(6)-methoxymethylsulfinyl-2-carbomethoxyaminobenzimidazole, 5(6)-naphth-2'-ylsulfinyl-2-carbomethoxyaminobenzimidazole, 5(6)-p-fluorophenylsulfinyl-2-carbomethoxyaminobenzimidazole, 5(6)-trifluoromethylmethylsulfinyl-2-carbomethoxyaminobenzimidazole, 5(6)-ethylsulfinyl-2-carbomethoxyaminobenzimidazole, 5(6)-n-propylsulfinyl-2-carbomethoxyaminobenzimidazole, 5(6)-n-butylsulfinyl-2-carbomethoxyaminobenzimidazole, 5(6)-(prop-en-1-ylsulfinyl)-2-carbomethoxyaminobenzimidazole, 5(6)-(prop-en-1-ylthio)-2-carbomethoxyaminobenzimidazole, 5(6)-(prop-yn-1-ylsulfinyl)-2-carbomethoxyaminobenzimidazole, 5(6)-(prop-yn-1-ylthio)-2-carbomethoxyaminobenzimidazole, 5(6)-methoxymethylthio-2-carbomethoxyaminobenzimidazole, 5(6)-methylthiomethoxy-2-carbomethoxyaminobenzimidazole, 5(6)-methylsulfinylmethoxy-2-carbomethoxyaminobenzimidazole, 5(6)-methoxymethoxy-2-carbomethoxyaminobenzimidazole, 5(6)-(2,2,3,3-tetrafluoropropylsulfinyl)-2-carbomethoxyaminobenzimidazole, 5(6)-trifluoromethylmethylsulfinyl-2-carbomethoxyaminobenzimidazole, 5(6)-methoxyethylsulfinyl-2-carbomethoxyaminobenzimidazole, and 5(6)-phenoxyethoxy-2-carbomethoxyaminobenzimidazole, or the corresponding 2-carbethoxyamino, 2-carbopropoxyamino- and 2-carbobutoxyamino compounds thereof for the substituted benzimidazole 2-carbamate utilized in the Examples, and utilizing the desired substituted isocyanate reactant (corresponding to OCNR⁸ defined above), the corresponding compounds of Formula I are prepared.

In the preceeding paragraph, the specific reaction utilized in the Examples above has been extended, in a general sense, to the preparation of other similar and related compounds, embraced by the present invention. It should be understood, however, that, with respect to any compound which has been prepared by the extension of this specific reaction sequence, it may be necessary or desirable to utilize solvents, reaction media, recrystallization media, reaction times or temperatures, etc., other than the ones given in the Examples above. This variation is deemed to be within the skill of those working in this art and will be apparent from a consideration of the particular reactants utilized and/or particular compound desired to be produced.

While the present invention has been described with reference to specific embodiments thereof, it should be understood by those skilled in this art that various changes may be made and equivalents may be substituted without departing from the true spirit and scope of the invention. In addition, many modifications may be made to adapt a particular situation, material or composition of matter, process, process step or steps, or then-present objective to the spirit of this invention without departing from its essential teachings.

What is claimed is:

1. A composition for controlling helminths in mammals comprising a pharmaceutically acceptable non-toxic excipient and an anthelmintically effective amount of a compound represented by the formula:

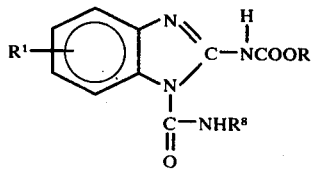

where
R is lower alkyl having 1 to 4 carbon atoms; $R^1$ is —$SOR^2$, —$SR^5$, —$OR^5$ or $M'(CH_2)_nMR^7$; $R^2$ is lower alkyl having from 1 to 6 carbon atoms, cycloalkyl having 3 to 7 carbon atoms, lower alkenyl or lower alkynyl having 3 to 6 carbon atoms, phenyl, benzyl or phenethyl; $R^5$ is lower alkenyl, lower alkynyl, benzyl or phenethyl; $R^7$ is lower alkyl having 1 to 4 carbon atoms or phenyl; M and M' are independently O, S,

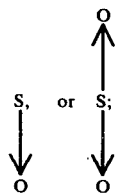

$n$ is 1–4; and $R^8$ is phenyl, benzyl, phenethyl, or lower alkyl having 1 to 12 carbon atoms and optionally substituted wih a —COOR group where R is lower alkyl having 1 to 4 carbon atoms; the $R^1$ substitution being at the 5(6)-position; or a pharmaceutically acceptable salt thereof.

2. The composition of claim 1 wherein $R^1$ is —$SOR^2$.
3. The composition of claim 1 wherein $R^1$ is —$SR^5$.
4. The composition of claim 1 wherein $R^1$ is —$OR^5$.
5. The composition of claim 1 wherein $R^1$ is —$S(CH_2)_nSR^7$.
6. The composition of claim 1 wherein $R^1$ is —$S(CH_2)_nOR^7$.
7. The composition of claim 1 wherein $R^1$ is —$O(CH_2)_nOR^7$.
8. The composition of claim 1 wherein $R^1$ is —$O(CH_2)_nSR^7$.
9. The composition of claim 1 wherein $R^1$ is

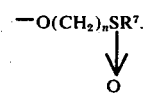

10. The composition of claim 1 wherein $R^1$ is

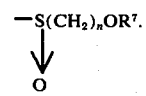

11. The composition of claim 1 wherein $R^2$ is lower alkyl.
12. The composition of claim 1 wherein $R^2$ is lower alkenyl.
13. The composition of claim 1 wherein $R^2$ is lower alkynyl.
14. The composition of claim 1 wherein $R^2$ is phenyl.
15. The composition of claim 1 wherein $R^1$ is phenylsulfinyl.
16. The composition of claim 1 wherein $R^2$ is benzyl or phenethyl.
17. The composition of claim 1 wherein $R^5$ is lower alkynyl.
18. The composition of claim 1 wherein $R^5$ is lower alkenyl.
19. The composition of claim 1 wherein $R^5$ is benzyl or phenethyl.
20. The composition of claim 1 wherein $R^8$ is lower alkyl optionally substituted with a —COOR group where R is defined in claim 1.
21. The composition of claim 1 wherein $R^8$ is phenyl.
22. The composition of claim 1 wherein $R^8$ is benzyl or phenethyl.
23. The composition of claim 1 wherein R is methyl.
24. The composition of claim 1 wherein said compound is 1-methylcarbamoyl-5-(6)-phenylsulfinyl-2-carbomethoxyaminobenzimidazole.
25. The composition of claim 1 wherein said compound is 1-ethoxycarbonylmethylcarbamoyl-5(6)-phenylsulfinyl-2-carbomethoxyaminobenzimidazole.
26. The composition of claim 1 wherein said compound is 1-phenylcarbamoyl-5(6)-phenylsulfinyl-2-carbomethoxyaminobenzimidazole.
27. The composition of claim 1 wherein said compound is 1-n-butylcarbamoyl-5(6)-methoxymethylsulfinyl-2-carbomethoxyaminobenzimidazole.
28. The composition of claim 1 wherein $R^8$ is lower alkyl.
29. The composition of claim 1 wherein $R^8$ is n-butyl.
30. The composition of claim 1 wherein said compound is selected from the group consisting of:

1-methylcarbamoyl-5(6)-phenylsulfinyl-2-carbomethoxyaminobenzimidazole,
1-ethoxycarbonylmethylcarbamoyl-5(6)-phenylsulfinyl-2-carbomethoxyaminobenzimidazole,
1-n-butylcarbamoyl-5(6)-phenylsulfinyl-2-carbomethoxyaminobenzimidazole,
1-phenylcarbamoyl-5(6)-phenylsulfinyl-2-carbomethoxyaminobenzimidazole, and
1-n-butylcarbamoyl-5(6)-methoxymethylsulfinyl-2-carbomethoxyaminobenzimidazole.

31. The composition of claim 1 wherein said compound is 1-n-butylcarbamoyl-5(6)-phenylsulfinyl-2-carbomethoxyaminobenzimidazole.

32. A method for controlling helminths in mammals which comprises administering an anthelmintically effective amount of a compound represented by the formula:

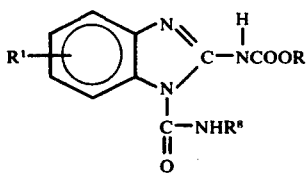

where
R is lower alkyl having 1 to 4 carbon atoms; $R^1$ is $-SOR^2$, $-SR^5$, $-OR^5$ or $M'(CH_2)_nMR^7$; $R^2$ is lower alkyl having from 1 to 6 carbon atoms, cycloalkyl having 3 to 7 carbon atoms, lower alkenyl or lower alkynyl having 3 to 6 carbon atoms, phenyl, benzyl or phenethyl; $R^5$ is lower alkenyl, lower alkynyl, benzyl or phenethyl; $R^7$ is lower alkyl having 1 to 4 carbon atoms or phenyl; M and M' are independently O, S,

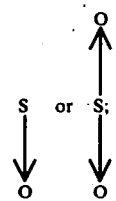

$n$ is 1–4; and $R^8$ is phenyl, benzyl, phenethyl, or lower alkyl having 1 to 12 carbon atoms and optionally substituted with a $-COOR$ group where R is lower alkyl having 1 to 4 carbon atoms; the $R^1$ substitution being at the 5(6)-position; or a pharmaceutically acceptable salt thereof.

33. The composition of claim 32 wherein $R^8$ is lower alkyl.

34. The composition of claim 32 wherein $R^8$ is n-butyl.

35. The composition of claim 32 wherein said compound is selected from the group consisting of:
1-methylcarbamoyl-5(6)-phenylsulfinyl-2-carbomethoxyaminobenzimidazole,
1-ethoxycarbonylmethylcarbamoyl-5(6)-phenylsulfinyl-2-carbomethoxyaminobenzimidazole,
1-n-butylcarbamoyl-5(6)-phenylsulfinyl-2-carbomethoxyaminobenzimidazole,
1-phenylcarbamoyl-5(6)-phenylsulfinyl-2-carbomethoxyaminobenzimidazole, and
1-n-butylcarbamoyl-5(6)-methoxymethylsulfinyl-2-carbomethoxyaminobenzimidazole.

36. The composition of claim 32 wherein said compound is 1-n-butylcarbamoyl-5(6)-phenylsulfinyl-2-carbomethoxyaminobenzimidazole.

* * * * *